United States Patent [19]

Newlove et al.

[11] Patent Number: 5,073,276

[45] Date of Patent: * Dec. 17, 1991

[54] POLYMER ARTICLE OF MANUFACTURE

[75] Inventors: John C. Newlove, Kingwood; Lee A. McDougall, Houston, both of Tex.; John R. Walker, Halifax; John R. Stockwell, Bradford, both of England

[73] Assignee: Exxon Research and Engineering Co., Florham Park, N.J.

[ * ] Notice: The portion of the term of this patent subsequent to Apr. 28, 2004 has been disclaimed.

[21] Appl. No.: 294,895

[22] Filed: Jan. 3, 1989

Related U.S. Application Data

[63] Continuation of Ser. No. 101,618, Nov. 13, 1987, abandoned, which is a continuation of Ser. No. 758,630, Jul. 11, 1985, abandoned.

[30] Foreign Application Priority Data

Nov. 25, 1983 [GB] United Kingdom ............... 8331546
Nov. 20, 1984 [WO] PCT Int'l Appl.... PCT/US84/01871

[51] Int. Cl.$^5$ .............................................. E21B 41/02
[52] U.S. Cl. ............................. 252/8.551; 252/8.552; 252/8.555; 166/304; 166/312
[58] Field of Search ................. 252/8.551–8.555; 166/279, 304, 312

[56] References Cited

U.S. PATENT DOCUMENTS

| 3,531,409 | 9/1970 | Seffens et al. | 252/8.55 |
|---|---|---|---|
| 3,921,636 | 11/1975 | Zaffaroni | 128/130 |
| 3,948,254 | 4/1976 | Zaffaroni | 128/130 |
| 3,993,072 | 11/1976 | Zaffaroni | 128/130 |
| 3,996,934 | 12/1976 | Zaffaroni | 128/130 |
| 4,660,645 | 4/1987 | Newlove et al. | 166/312 |
| 4,670,166 | 6/1987 | McDougall et al. | 166/280 |

Primary Examiner—Robert J. Hill, Jr.
Attorney, Agent, or Firm—R. L. Graham

[57] ABSTRACT

A solid polymeric body comprising a polymer matrix containing a substantially water-insoluble reagent leachable into a substantially hydrocarbon liquid environment, the matrix being reagent permeative and the body preferably having a softening point substantially above that of the temperature of the liquid fluid environment in which it is to be employed. The body is useful for the introduction of an additive reagent into a substantially liquid hydrocarbon such as crude and refined oils.

12 Claims, No Drawings

POLYMER ARTICLE OF MANUFACTURE

This is a continuation of application Ser. No. 101,618, filed Nov. 13, 1987 (now abandoned) which is a continuation of application Ser. No. 758,630, filed July 11, 1985 (now abandoned).

FIELD OF THE INVENTION

This invention relates to a polymeric body useful for introduction of an additive into a substantially hydrocarbon liquid. More particularly this invention relates to a bead containing an additive which is leachable into an oleaginous hydrocarbon liquid (both crude and refined) and the method of utilizing the bead to introduce the additive in useful amounts into the liquid hydrocarbon.

BACKGROUND OF THE INVENTION

The recovery of oil and gas from underground geological formations is of great importance in modern society which uses vast amounts of fossil fuels for its essential energy. The individual well productivity declines over a period of time because of a number of factors including changes in reservoir fluid characteristics, depletion of reservoir energy, decreasing permeability of the formation to the oil, the gradual dissipation of the expanding pressure transient, contamination of the well bore, reduced permeability of the oil through the region immediately surrounding the well bore and reduction of the internal diameter of the well pipe.

The response to the declining productivity was the development of numerous techniques which has become collectively known as well workover and stimulation. The concept of fracturing or formation breakdown has been recognized to play a very important role in the application of these oil production enhancement techniques including stimulation, acidizing, water injection and cementing of the formation.

Hydraulic fracturing has found wide usage as a well stimulation procedure for creating deep-penetrating fractures (both horizontal and vertical) that provide high capacity channels for flow from deep within the producing formation to the well as well as for overcoming damaged matrix permeability surrounding a wellbore. In order to produce gas or liquids from a well at a higher rate following a hydraulic fracturing treatment, the reservoir must contain enough fluids in place and the formation must not have regions of severe permeability reduction particularly in regions adjacent to the well. Early experimental work in shallow wells demonstrated that a hydraulically formed fracture tends to heal—that is, to lose its fluid carrying capacity after the parting pressure is released—unless the fracture is propped. Typical propping agents for retaining the integrity of the fractures are nutshells, plastic beads, aluminum spacers, glass beads, sand and urea prills.

Proppants thus provide a means for meeting the objective of the fracturing which is to increase the well production by preventing collapse of the formation and resultant decrease in fluid permeability.

Another cause of declining well production is caused by paraffin deposition from the crude oil onto the inner walls of the production tubing and equipment.

Paraffin is a reservoir produced group of straight-chain alkanes that contain more than 15 to more than 80 carbon atoms. The melting point of the paraffin increases as the size of the molecule increases. Paraffin is deposited in the form of crystalline solids which may collect on the interior of the tubing and flowlines, slowly choking off production. Paraffin deposits have also caused the breaking of pump rods. In some cases, paraffin deposits have caused plugging of formations during stimulation treatments. Paraffin has also been blamed for the difficulty in pumping crude oil at cool temperatures.

One method of handling paraffin deposition is to mechanically remove the paraffin. There are several mechanical methods for removing deposited paraffin from tubing, flowlines and pipelines which include rod scrapers, free-floating pistons, etc. The major advantage of mechanically removing paraffin is that positive cleaning is assured, however, it is limited due to time and equipment involved, costly and has the danger and difficulty inherent in retrieving tools lost in the hole during the cleaning operation.

Other methods of cleaning include:

(1) thermal methods, using bottomhole heaters, circulation of hot oil, water or steam, and heat-liberating chemicals; and, chemical including the use of paraffin solvents, dispersants and detergents and crystal modifiers whereby the latter prevents paraffin deposition by disrupting the nucleation, agglomeration and/or deposition of the paraffin crystals environment. At present the chemical reagent is injected into the desired location but it can be difficult to supply it uniformly to the optimum location, for instance in the permeable, oil bearing, mineral formation. Also it is necessary to inject the reagent continuously or repeatedly since it is soluble in the produced fluid and so is rapidly removed from the point of injection.

As indicated it is known to introduce reagents downhole during fracturing and other well stimulation processes. Traditionally this is done by forcing a solution of the reagent down the hole and into the formation, whereupon it becomes absorbed onto the formation and is released slowly from it. Unfortunately the rate of release is variable and generally is quite fast.

It is known to force beads of ethylene-vinyl acetate copolymers into the formation, but they are generally too large to get into the fractures formed in the formation and smaller beads would dissolve too rapidly. Also the beads are rather soft.

Another approach to overcoming the paraffin deposition in the recovery of crude oil is by adding to the oil a polymer having pendant polar and non-polar moieties, such as a partially hydrolyzed ethylene-vinyl acetate copolymer, whereby the deposition of wax from the oil is inhibited (see U.S. Pat. No. 3,693,720 wherein the inhibitor is added to the crude petroleum oil before the temperature of said oil decreases to a wax-deposition temperature).

It is known from British Patent Specification 1,290,554 to inhibit scale formation downhole by supplying downhole a solid linear carboxylic polymer having low molecular weight and in which the carboxylic groups are neutralized by an alkaline earth or other insolubilizing cation to an extent such that the polymer has a controlled low solubility in water. It is stated in that specification that water soluble scale inhibitors may also be supplied downhole with the substantially insoluble polymer.

It is an object of this invention to provide an article and its use to enhance the production of hydrocarbons from geological reservoirs, more particularly from fractured formations.

It has been an additional object to devise a composition for providing controlled release of a reagent downhole, in a pipeline, in other oil-containing environments or fluids.

SUMMARY OF THE INVENTION

It has been discovered that it is possible to provide for the introduction of an additive reagent into a liquid hydrocarbon by providing solid polymeric bodies each comprising a polymeric matrix containing a substantially water insoluble reagent such as a wax crystal modifier, demulsifier, scale inhibitor, corrosion inhibitor, biocide, ashless dispersant, antioxidant and mixtures thereof. These bodies are, in use, positioned at a location where it is desired to release the reagent into the substantially hydrocarbon fluid and, upon contact with fluid in this location, active reagent is released into the fluid.

Thus in accordance with this invention there is provided a solid polymeric body comprising a polymer matrix containing a substantially water-insoluble reagent leachable into a substantially hydrocarbon liquid environment, said matrix being reagent permeative and the said body preferably having a softening point substantially above that of the temperature of the liquid fluid environment in which it is to be employed and optimally having a leach rate in which fifty percent of the reagent is leached from the bead in from 3 months to 3 years by the fluid environment.

The object of this invention has been realized in specific form by beads comprising a copolymeric matrix of methylmethacrylate and methacrylic acid containing the behenyl half ester of a $C_{24}$-$C_{28}$ alkenyl succinic anhydride polymer and having a diameter ranging from 0.2 to 1 mm. Such beads when introduced downhole in a hydraulic fracturing operation were found to inhibit paraffin wax deposition.

DETAILED DESCRIPTION OF THE INVENTION

Each of the solid polymeric bodies may consist solely of a polymeric matrix containing the reagent or may contain a region, generally an outer region, of polymeric material having a lower rate of reagent permeation than that of the interior region and substantially free of reagent. The polymer of such an outer shell may be of the same material as the matrix or may be different, and will be selected having regard to the release properties required from the polymeric bodies. Matrix containing reagent may be of uniform composition throughout its body or its composition may vary, for instance having a different polymer composition in its outermost portions from its core portion. By appropriate selection of the polymeric materials for forming the bodies and the distribution of reagent within the bodies it is possible to control the rate and duration of release of reagent into the fluid while retaining the physical (structural) integrity of the polymeric matrix.

It is this polymeric property of reagent permeativity which makes possible the transfer of the reagent from the body into the substantially hydrocarbon liquid in contact with the surface of the body. During and after the leaching of the reagent from the reagent permeative matrix of the body, the polymeric matrix retains its structural integrity which is in marked contrast to the approach taught in Egypt. J. Pharm. Sci., 19 No. 1-4, pages 143-62, 1980 in an article by A. Kassem et al entitled Formulation and Evaluation of Controlled Dissolution Phenobarbitone Macromolecular Products Employing In Situ Suspension Polymerization With Methylmethacrylate wherein the reagent coated beads were compressed into a body which upon reagent dissolution in the physiological aqueous fluids broke down the body into its component beads thus fully destroying the structural integrity of the compressed body.

The polymeric bodies are preferably particles. The particle size is generally at least 10 microns and preferably at least 50, and usually at least 100, microns since small particles can be difficult to handle and to position permanently in their desired environment. The particle size is generally less than 2 mm and preferably less than 1 mm, since large particles also may be difficult to position in their desired environment. Best results are generally obtained with a particle size of from 50 microns to 1 mm. The particles may have irregular shape and sizes, for instance as a result of having been made by crushing, but preferably the particles are of substantially spherical or other uniform shape.

When being used in fracturing, the particles preferably have a size and hardness and/or resistance to flow such that they can be used in sand packing and will not be significantly degraded by the sand. The particle size distribution will be selected so that a pack of controlled permeability to fluid flow is formed and such that the particles have a controlled leach rate as set forth earlier.

The reagent must be substantially water insoluble, and so must partition into an organic phase of substantially water-insoluble polymerizable monomer or monomer mixture in preference to a water phase. The reagent may be in its active form or it may be in a blocked water-insoluble form from which an active form may be released during use and that may be water soluble.

The reagent may be dissolved in the polymeric matrix but preferably at least some, and generally substantially all, of the reagent is dispersed in the matrix. The softening point of the matrix should be above ambient temperatures encountered in use.

The reagent may be any active reagent that is usefully administered to and is soluble in refined or crude oil, or that is any blocked reagent that is water insoluble but which, upon contact with water or oil, will release a water soluble or water insoluble reagent that is useful in the substantially hydrocarbon fluid. The reagents are usefully selected from wax crystal modifiers, demulsifiers, scale inhibitors, corrosion inhibitors, biocides, dispersants, antioxidants and mixtures thereof.

(A) WAX CRYSTAL MODIFIERS

These reagents, usefully introduced in at least a wax deposit inhibiting amount to the refined and crude oil, are represented by oil-soluble polymers having pendant polar and non-polar moieties and oil-soluble polymeric materials having long linear side chains. The oil-soluble copolymers having pendant polar and non-polar moieties are represented by the formula

wherein X is a non-polar moiety, Y is a polar moiety, R is hydrogen, an alkyl, aryl, aralkyl, or alkaryl moiety, m is 1.5-3, n is 0.1-0.8, p is 0.01-0.5, $m/(m+n+p)$ is 0.65-0.97, $p/(n+p)$ is 0.1-0.85, q is 2 to 500, and the molecular weight $M_w$ of said polymer is 500-100,000.

The above polymer may typically be a polymer having a molecular weight $M_w$ of 500-100,000, preferably 1,000-10,000, commonly 1,500-4,000, say 2,000, and characterized by a long straight backbone chain on which there may be pendant moieties X and Y.

In the above copolymer, the moiety $+CH_2CHX+_n$ may be derived from an alpha-olefin including ethylene, propylene, butene-1, styrene, 3-phenyl-1-propene, octene-1, etc. Preferred alpha-olefins may be the $C_2$-$C_{30}$ alpha-olefins and most preferred is ethylene. When the alpha olefin is propylene, the formula $+CH_2CHR+_m$ may be

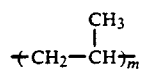

in which R is $-CH_3$. When the alpha olefin is ethylene, the formula may be $+CH_2-CH_2+_m$. The carbon atoms may bear insert substituents (i.e. in place of the hydrogen atoms) including alkyl, cycloalkyl, aryl, alkaryl, aralkyl, etc., moieties.

In the above copolymer, the moiety $+CH_2CHX+_n$ may be derived from an alpha-olefin which bears nonpolar moiety X. The non-polar X moiety may be characterized by the fact that it does not contain a hydrogen atom active in the Zerewitinoff test for active hydrogen. Typically, the non-polar moiety will contain atoms of carbon, nitrogen, sulphur, phosphorous, boron, oxygen, etc. The polar moiety Y may be a moiety containing carbon, oxygen, sulphur, nitrogen, phosphorous boron or their congeners. The Y moiety contains a hydrogen atom which is capable of participating in hydrogen bonding. A typically useful wax crystal modifier is a partially hydrolyzed ethylene vinyl acetate copolymer having a molecular weight $M_w$ of 1,500–4,000. For a more complete description of these copolymers reference should be made to U.S. Pat. No. 3,693,720 which by that act is fully incorporated herein and to which reference should be made.

Another class or wax crystal modifiers are the oil-soluble polymeric materials having long linear side chains as described in U.S. Pat. No. 3,854,893 and include condensation polymers of dicarboxylic acid or anhydride, polyol and monocarboxylic acid; addition polymers of unsaturated esters, or long chain alpha monoolefins, or copolymers of said olefins with said unsaturated ester; polystyrene acrylated with long chain fatty acids; and, mixtures thereof. Particularly useful are the copolymers of $C_{18}$ to $C_{46}$ olefin with a $C_4$ to $C_{44}$ straight chain alcohol per molar proportion of said dicarboxylic acid. Representative of these particularly useful copolymers are the esters formed by reaction between the reaction product of an olefin and maleic anhydride with a long chain (typically $C_{16}$–$C_{28}$) aliphatic alcohol, and most preferably the reagent is the behenyl ester of alkenyl succinic anhydride having a molecular weight of from 3000 to 10,000 formed by polymerizing a $C_{22}$–$C_{28}$ alpha-olefin with maleic anhydride.

Other wax crystal modifiers known for use as pour point depressants are represented by: low molecular weight $C_{16-24}$ alkyl acrylates and copolymers with 4-vinyl pyridine, acrylamide, maleic acid, or dimethylaminoethyl acrylate; copolymers of alkyl fumarate and vinyl acetate; copolymers of ethylene or other olefins with vinyl alkylate (such as acetate, stearate or laurate); and, copolymers of alpha-olefins with maleic anhydride or other dicarboxylic group, for instance to form alkenyl succinic anhydride and the reaction products of such materials with long chain epoxides and long chain alcohols.

(B) DEMULSIFIERS

These reagents which can be introduced into a fractured subterranean oil bearing formation in accordance with this invention are usefully introduced to inhibit emulsification of the crude oil with formation water, water flood injection water and/or water introduced by such processes as steam stimulation. These oil-soluble reagents include polyoxyalkylene ether and polyalkylene surfactants formed from the alkoxylation of hydrocarbon soluble alkyl phenols, phenolic resins, alcohols, glycols, amines, organic acids, carbohydrates, mercaptans, and partial esters of polybasic acids.

(C) SCALE INHIBITORS

Since scale inhibitors are water soluble each is introduced into a fractured subterranean formation in accordance with this invention as the reagent in a blocked form such that the reagent upon contact with water, as by leaching from the polymeric matrix, is converted into a water soluble active form, e.g. as a result of hydrolysis or ion exchange. Suitable blocked forms are fatty acid esters and salts.

Typical examples of blocked scale inhibitors are the salts formed by the reaction of hydrophobic amines with low molecular weight polycarboxylic acids or polyphosphonic acids, e.g. a tri($C_6$–$C_{10}$ alkyl) ammonium salt of: polyacrylic acid having a $M_w$ of from 1,000 to 5,000; or dihexylene triamino pentakis methylene phosphonic acid. It is believed that the latter reagent also has activity as a corrosion inhibitor.

(D) CORROSION INHIBITORS AND BIOCIDES

Useful reagents which have the property of corrosion inhibition and/or biocidal activity include both oil-soluble and water-soluble materials. The latter must be incorporated into the polymeric matrix in blocked form.

Typical examples of oil soluble corrosion inhibitors and/or biocides are amines, diamines, fatty amines, polyamines, alkoxylated amines, hydrogenated fatty amines, amides, fatty acid amides, imidazolines, and trimer acids.

Typical examples of water soluble corrosion inhibitors and/or biocides are quaternary amines and quaternized imidazolines each of which can be individually blocked by reaction with oleophilic fatty acids to form water insoluble salts whereby it becomes useful in the present invention.

The reagents may also be materials of value in fuels and lubricating oils, for instance ashless dispersants or antioxidants. A filter bed through which such fluids or oils pass may contain or consist of the particles containing such reagents.

(E) ASHLESS DISPERSANTS

As used herein, the terminology "ashless dispersant" is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and are generally characterized by substantially hydrocarbon constituents containing an average of 50 to 250 aliphatic carbon atoms.

A preferred class of ashless dispersants are the nitrogen-containing dispersant additives which include mineral oil-soluble salts, amides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a mono-carboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1.

Primarily because of its ready availability and low cost, the hydrocarbon portion of the mono-, or dicarboxylic acid or anhydride is preferably derived from a polymer of a $C_2$ to $C_5$ monoolefin, said polymer monoolefin generally having between 50 and 250 carbon atoms. A particularly preferred polymer is polyisobutylene.

Polyalkyleneamines are usually used to make the non-metal-containing dispersant. These polyalkyleneamines include diethylenetriamine, tetraethylenepentamine, dipropylenetriamine, octaethylenenonamine, and tetrapropylenepentamine. Highly useful mixtures of alkylene polyamines approximating tetraethylene pentamine are commercially available.

Representative dispersants are formed by reacting about one molar amount of an oil-soluble polyisobutenyl succinic anhydride with from about one to about two molar amounts of tetraethylene pentamine or with from about 0.5 to 1 moles of a polyol, e.g. pentaerythritol.

It is possible to modify the ashless dispersants generally by the addition of metals such as boron in order to enhance the dispersancy of the additive.

(G) ANTIOXIDANTS

As used herein, antioxidants are oil-soluble oxidation inhibitors and generally represented by the additives for lubricating oils which include phenols, amines, sulphurized phenols, alkyl phenothiazines, and zinc dihydrocarbyl phosphorodithioates, e.g. zinc di-n-propyl dithiophosphate.

POLYMERIC BODY

The polymeric matrix is reagent permeative and preferably has a softening point as measured by a temperature-graded hot bar of above 30° C. and most preferably is above 60° C., often up to 120° C. The combination of the reagent and the polymeric matrix must be such that the reagent is released into surrounding fluid at the desired time and rate either as a result of the fluid permeating through the matrix to dissolve the reagent or as a result of the reagent permeating through the matrix to dissolve into the fluid, or both.

The polymer of the matrix is preferably formed mainly of acrylic alkyl ester or styrene or acrylonitrile or a mixture thereof. Suitable acrylic esters are alkyl acrylates and methacrylates where the alkyl group contains from 1 to 6 and preferably 1 to 3 carbon atoms. The ester is preferably a methacrylate and the preferred ester is methyl methacrylate. The polymer is preferably formed mainly of methyl methacrylate or a blend of methyl methacrylate and styrene. Small amounts of other polymerizable monomers, for instance up to 40%, generally below 20% by weight and preferably below 10% by weight, may be included provided they do not deleteriously affect the properties of the polymer. Other suitable monomers include hydroxyalkyl acrylates and methacrylates, maleate esters, vinyl esters, dialkylaminoalkylacrylates and methacrylates and crosslinking monomers such as glycol dimethacrylate. It is particularly preferred to include carboxylic monomers such as acrylic or methacrylic acid which are useful in modification of the rate of reagent permeation from the polymeric body when these monomers are incorporated into the monomer mixture, they tend to migrate toward the outer layers of the polymerizing body due to their hydrophilic nature relative to the reagents. The result is a body having a lower rate of reagent permeation through its outer region than that of the interior region. This approach provides a means of controlling the leach rate of the reagent from the body.

The amount of reagent is generally at least 5% by weight of the total body in order to maximize the amount of reagent introduced into the desired location. It can be difficult to produce bodies containing very high amounts of reagent and so the amount is generally not more than 50%, and usually not more than 30%, by weight of the total body. The preferred reagent amount is usually 10 to 30% by weight of the total body.

The invention has widely diverse applications since it makes possible a controlled release of reagent into liquids in a uniform manner and over extended time periods. It makes possible the release of certain reagents from previously non- or difficulty accessible and diverse points such as in an oil bearing mineral formation one or more miles underground and in the flow path of a circulating engine lubricant.

This invention provides a method for the controlled introduction of a reagent into a substantially hydrocarbon liquid, generally a circulating liquid, which method comprises the steps of:

(a) placing solid polymeric bodies, each body comprising a polymeric matrix containing at least one substantially water insoluble reagent in a liquid, generally flowing, substantially hydrocarbon fluid; and (b) leaching out said reagent from said bodies at a controlled and predetermined rate into said liquid fluid, said fluid preferably containing oil.

In a preferred manner the invention provides a method of recovering a crude petroleum oil containing waxy components, from a reservoir wherein the oil is at a temperature above its wax deposition temperature which comprises:

a. passing a portion of said crude petroleum oil from said reservoir to a first central collection point, i.e. the well bore;

b. passing said oil from said first central collection point to a second collection point, i.e. the well head at a temperature below the wax deposition temperature of said oil whereby the temperature of said oil decreases and passes through a wax-deposition temperature at which the waxy components begin to precipitate and to deposit on surfaces with which said oil comes in contact as it passes to said second collection point;

c. collecting said crude petroleum oil at said second collection point; and, d. adding to said portion of crude petroleum oil before it passes to said first central collection point a wax-depositon inhibiting amount of a wax crystal modifier reagent by flowing said portion through a particulate grid of proppant and solid polymeric bodies each body comprising a polymeric matrix containing a substantially water-insoluble wax deposition inhibitor reagent, said reagent optimally the behenyl half ester of a $C_{24}$–$C_{28}$ alkenyl succinic anhydride polymer and contained in said matrix in an amount ranging from 5 to 50 weight percent of the total weight of said body.

The method of making the bodies of polymeric matrix containing substantially water-insoluble reagent involves forming a dispersion in an aqueous medium of particles of reagent and liquid polymerizable material and polymerizing the polymerizable material while maintaining the particles dispersed in the medium. The polymerization results in the formation of a suspension of polymer beads each containing reagent. The beads may be filtered or otherwise separated from the aqueous medium. They may be washed and dried.

The aqueous medium will generally include a polymeric stabilizer suitable for suspension polymerization. This is often a hydrophilic polymer that is swellable in, and usually soluble in, the aqueous medium. The hydrophilic dispersing stabilizer may be a naturally occurring or modified naturally occurring polymer, such as a hydroxyethyl cellulose, or a synthetic water soluble polymer, for instance polyvinyl alcohol or polyethylene oxide but preferably is a synthetic carboxylic acid containing polymer, most preferably polyacrylic acid having a molecular weight in the range 1 million to 10 million. The amount is generally 0.2 to 5% weight of the water.

In order to obtain uniform and fine distribution of the reagent in the polymeric matrix, it is necessary for the reagent to be monomer-wetting rather than water-wetting and preferably the reagent is in liquid form during polymerization of the matrix. It could be introduced as a solution in toluene or other suitable organic solvent but this would have the disadvantage of incorporating solvent in the matrix. Preferably therefore the reagent is one that dissolves into the polymerizable material, if necessary as a result of being heated. For instance it may be insoluble in the polymerizable material at ambient temperatures but may become soluble upon heating to a temperature between 50° and 80° C., in which event the dispersion of the particles of reagent and liquid polymerizable material is formed at such a temperature. The elevated temperature may be such that the reagent is then truly molten or may be such as to promote solubility of the reagent in the polymerizable material.

Preferably a homogeneous blend is formed of the reagent and the monomer or monomers, dispersed into the aqueous medium by stirring and polymerization is initiated by using an oil soluble thermal initiator.

The following are examples of the invention.

EXAMPLE 1

The behenyl half ester of a $C_{24}$–$C_{28}$ alkenyl succinic anhydride polymer produced generally according to the procedure set forth for preparation of Polymer B disclosed in U.S. Pat. No. 3,854,893 was supplied as a solution in toluene, and this solvent was evaporated to leave a waxy solid. This wax, i.e. the reagent, was insoluble in methyl methacrylate monomers at temperatures up to 50° C. A monomer solution containing the wax reagent was formed of 85 g methyl methacrylate, 5 g methacrylic acid and 10 g of the wax by heating all to 65° C., at which temperature the wax dissolved into the monomers. The resultant solution was then dispersed in 200 g water containing 3 g polyacrylic acid (molecular weight about 2 million) as a dispersing stabilizer of the monomer droplets during polymerization in a one liter enclosed vessel provided with a stirrer for controlled agitation of the contents within the vessel. Under constant agitation 1 g of azodiisobutyronitrile as the polymerization inhibitor was added. Suspension polymerization was continued with constant agitation for two hours after which time the product within the vessel consisted of a suspension of small polymeric beads in the aqueous medium. These beads were separated from the aqueous medium, washed and dried to give free flowing beads of from 0.2 to 1 mm in diameter with 10% by weight of the waxy ester polymer reagent dispersed in the polymeric matrix.

Since the behenyl ester wax reagent is very soluble in hexane, to demonstrate the retardation of solubility by the invention the produced beads were stirred in hexane at 35° C and the amount of wax released recorded. The following results were obtained.

| % of Total Wax Released at 35° C. | Time Hours |
| --- | --- |
| 40 | 1 |
| 42 | 2 |
| 45 | 3 |
| 49 | 4 |
| 53 | 5 |

EXAMPLE 2

When the above process was repeated using 10 g wax reagent (as above described), 5 g acrylic acid, 5 g methacrylic acid and 80 g methyl methacrylate followed by neutralization with sodium hydroxide dispersion, the beads have a shell containing a high proportion of sodium polyacrylate and have slower release properties compared to the release properties of the beads of Example 1 when the polymerizate dispersion was similarly neutralized. In particular, after 5 hours at 35° C. in hexane as in Example 1, only 25% of the wax was released.

EXAMPLE 3

To produce a polymeric body according to this invention containing a leachable scale inhibitor, the polymerization mixture will be 85 g of methyl methacrylate, 5 g methacrylic acid and 10 g tri($C_6$–$C_{10}$ alkyl) ammonium salt of a poly(acrylic acid) having a Mw of 1,000 to 5,000. The polymerization mixture is to be polymerized under the conditions of Example 1.

EXAMPLE 4

In order to produce a polymeric body according to this invention containing a leachable corrosion inhibitor reagent, the procedure of Example 3 is to be followed except that the 5 g of methacrylic acid is replaced with 5 g of dimethylaminoethyl acrylate, the 10 g of the ammonium salt is replaced with 10 g of the equimolar reaction product of tall oil fatty acid and diethylene triamine and the anionic dispersing stabilizer is changed to 3 g of the methyl chloride quaternary salt of poly (di-methylaminoacrylate) of about 1 million Mw.

EXAMPLE 5

In order to produce a polymeric body according to this invention containing a leachable demulsifier, the procedure of Example 3 is followed except that the following monomer mixture is used: 65 g methyl methacrylate, 20 g styrene, 5 g methacrylic acid and 10 g of an oxyalkylated phenol formaldehyde resin of 2000 Mw where the weight ration of ethylene oxide to propylene oxide to resin is 0.5:0.5:1.5.

EXAMPLE 6

In order to produce a polymeric body according to this invention containing a leachable ashless dispersant, the procedure of EXAMPLE 1 is followed except that the wax is replaced with the equimolar reaction product of polyisobutenyl succinic anhydride having a Mw of about 900 and pentacrythritol.

EXAMPLE 7

The effectiveness of the present invention in the inhibition of wax deposition from a crude oil was shown by comparison of the product of Example 1 with a solution of the reagent of Example 1 on a crude oil (in which the aforesaid reagent has shown measurable wax deposition inhibiting activity) using the following procedure. 0.03 weight parts of active ingredient was introduced into 100 weight parts of crude petroleum oil. The mixture was placed within a test cell containing a preweighed, removable standard water chilled deposition steel plate, a stirrer thermometer, and an electrical heater. The test cell was placed in an insulated bath together with an identical reference cell containing the reagent solution treated base crude oil. The temperature of the oils in both cells was maintained at 2° to 5.5° C. above the known cloud point temperature of the oil (as determined by ASTM D-97-57). The test was continued for 6 hours and then each deposition plate was removed, and weighed. The amount of wax deposit on each plate was for measureable activity the same.

EXAMPLE OF USE

The solid particles of the present invention can be used to inhibit paraffin deposition from waxy crude oils by placing them downhole with the proppant sand during the course of a fracturing operation.

To effect the placement of the particles of the invention a fracturing operation is carried out as follows. A fracturing fluid is prepared by gelling a 2% solution of potassium chloride with hydroxy propyl guar cross linked with a transition metal complex. As the fluid is pumped downhole 8 lbs/1000 gals of 20-40 mesh sand mixed with 5% of the beads of the invention are added to serve as a proppant in the fractures formed in the producing formation. Pump pressure is increased above the fracture gradient of the rock formation and the fluid carries the proppant mixture into the fractures. The well is then shut in for 24 hours to allow the guar gel to degrade to a low viscosity solution. The well is allowed to flow back and the fracturing fluid is recovered leaving the proppant mixture of sand and polymer beads behind.

As the produced oil flows through the proppant pack past the beads the wax deposition inhibitor slowly leaches out and deposition is inhibited in the well bore and the flow lines as the oil cools and production is maintained at a high level without wax blockage.

As used herein % by weight is based on the total weight of the body, polymer composition, water or bead, respectively.

What is claimed is:

1. A particulate treating material for an environment including a hydrocarbon liquid, each particle of the material comprising:
   (a) a body composed of a copolymer prepared by suspension polymerization of a monomer mixture of
      (i) a first monomer selected from the group consisting of acrylic alkyl esters, styrene, acrylonitrile, and mixtures thereof;
      (ii) a second monomer selected from the group consisting of methacrylic acid, hydroxyalkyl acrylates, hydroxyalkyl methacrylates, dialkylaminoalkyl acrylates, dialkylaminoalkyl methacrylates, and mixtures thereof;
   said copolymer being insoluble in hydrocarbon liquid, having a softening point above 30° C., having structural integrity, internal porosity, and a particle size of at least 100 microns and less than 2 millimeters; and
   (b) a reagent soluble in hydrocarbon liquid and being dispersed in said body, said reagent constituting at least 5 wt % and not more than 30 wt % based on the combined weights of the body and reagent, said reagent being added to, and soluble in, the monomer mixture and insoluble in the copolymer and being selected from the group consisting of scale inhibitors, corrosion inhibitors, biocides, foamers, and oxygen scavengers, and being leachable, at least in part, by a hydrocarbon liquid permeating said body, said body retaining its structural integrity without the reagent.

2. The particulate treating material of claim 1 wherein the first monomer is selected from the group consisting of alkyl acrylates and alkyl methacrylates wherein the alkyl group contains from 1 to 6 carbon atoms.

3. The particulate treating material of claim 2 wherein the first monomer is methyl methacrylate.

4. The particulate treating material of claim 1 wherein the monomer mixture further includes an effective amount but less than 10 wt % of acrylic acid or methacrylic acid based on the weight of the monomers to provide an outer region of reduced permeability compared to the particle region within the outer region.

5. The particulate treating material of claim 4 wherein the monomer mixture comprises a major weight proportion of the first monomer.

6. The particulate treating material of claim 5 wherein the first monomer is methyl methacrylate.

7. The particulate treating material of claim 1 wherein the first monomer is a blend of methyl methacrylate and styrene.

8. A particulate treating material for treating environments containing a hydrocarbon liquid wherein each particle comprises a solid copolymer body of structural integrity and having a particle size between 100 microns and 2 millimeters and a softening point above 30° C., said copolymer body being formed by aqueous suspension polymerization of
   (a) a monomer mixture comprising
      (i) a first monomer selected from the group consisting of alkyl acrylic esters, styrene, and mixtures thereof,
      (ii) a second monomer selected from the group consisting of a methacrylic acid, hydroxyalkyl acrylates, hydroxyalkyl methacrylates and dialkylaminoalkyl acrylates, dialkylaminoalkyl methacrylates, and mixtures thereof; and (b) a water-insoluble, hydrocarbon liquid-soluble reagent dissolved in the monomer mixture, and being insoluble in the polymerized copolymer, whereby the reagent is dispersed throughout the copolymer body, said reagent being leachable from the body by the hydrocarbon liquid, at least in part, permeating the body, each body retaining its structural integrity with the reagent leached therefrom.

9. The particles of claim 8 wherein the first monomer is methyl methacrylate.

10. The particles of claim 8 wherein concentration of the second monomer is sufficient to produce the copolymer but does not exceed 20 wt % of the copolymer.

11. The particulate treating material of claim 8 wherein the monomer mixture further includes an effective amount but less than 10 wt % of acrylic acid or methacrylic acid based on the weight of the monomers to provide an outer region of reduced permeability compared to the particle region within the outer region.

12. The particles of claim 8 wherein the reagent is the behenyl half of a $C_{24}$-$C_{28}$ alkenyl succinic anhydride polymer.

* * * * *